US008649000B1

United States Patent
Anderson (10) Patent No.: US 8,649,000 B1
(45) Date of Patent: Feb. 11, 2014

(54) WHISPERING GALLERY OPTICAL RESONATOR SPECTROSCOPIC PROBE AND METHOD

(75) Inventor: Mark S Anderson, La Crescenta, CA (US)

(73) Assignee: The United States of America as Represented by the Administrator of the National Aeronautics and Space Administration, Washington, DC (US)

( * ) Notice: Subject to any disclaimer, the term of this patent is extended or adjusted under 35 U.S.C. 154(b) by 264 days.

(21) Appl. No.: 13/277,954

(22) Filed: Oct. 20, 2011

Related U.S. Application Data (60) Provisional application No. 61/407,177, filed on Oct. 27, 2010.

(51) Int. Cl.
*G01J 3/00* (2006.01)

(52) U.S. Cl.
USPC .......................................................... 356/51

(58) Field of Classification Search
USPC .................................. 356/51, 301
See application file for complete search history.

(56) References Cited

U.S. PATENT DOCUMENTS

| | | | | |
|---|---|---|---|---|
| 4,829,537 | A * | 5/1989 | Baer | 372/66 |
| 4,852,955 | A | 8/1989 | Doyle et al. | |
| 5,343,490 | A * | 8/1994 | McCall | 372/94 |
| 6,141,095 | A | 10/2000 | Allen et al. | |
| 6,777,244 | B2 * | 8/2004 | Pepper et al. | 436/165 |
| 6,850,323 | B2 * | 2/2005 | Anderson | 356/301 |
| 7,693,369 | B2 * | 4/2010 | Fan et al. | 385/32 |
| 8,092,855 | B2 * | 1/2012 | Armani et al. | 427/2.13 |
| 8,108,943 | B2 * | 1/2012 | Anderson | 850/30 |
| 8,493,560 | B2 * | 7/2013 | Shopova et al. | 356/301 |
| 2002/0068018 | A1 * | 6/2002 | Pepper et al. | 422/82.05 |
| 2002/0079453 | A1 * | 6/2002 | Tapalian et al. | 250/343 |
| 2002/0105641 | A1 * | 8/2002 | Anderson | 356/301 |
| 2005/0128476 | A1 | 6/2005 | Zhao | |
| 2007/0237460 | A1 * | 10/2007 | Fan et al. | 385/39 |
| 2008/0225268 | A1 * | 9/2008 | Sigalas et al. | 356/36 |
| 2009/0214755 | A1 * | 8/2009 | Armani et al. | 427/2.13 |
| 2010/0231903 | A1 | 9/2010 | Sumetsky | |
| 2010/0243448 | A1 | 9/2010 | Maurer et al. | |
| 2010/0264300 | A1 | 10/2010 | Savchenkov et al. | |

OTHER PUBLICATIONS

L. K. Ausman and G. C. Schatz, The Journal of Chemical Physics. 129, 054704, 2008). Whispering Gallery Mode Resonators: Surface Enhanced Raman Scattering Without Plasmons.

* cited by examiner

*Primary Examiner* — Roy M Punnoose
(74) *Attorney, Agent, or Firm* — Mark Homer (57) ABSTRACT

Disclosed herein is a spectroscopic probe comprising at least one whispering gallery mode optical resonator disposed on a support, the whispering gallery mode optical resonator comprising a continuous outer surface having a cross section comprising a first diameter and a second diameter, wherein the first diameter is greater than the second diameter. A method of measuring a Raman spectrum and an Infra-red spectrum of an analyte using the spectroscopic probe is also disclosed.

22 Claims, 4 Drawing Sheets

WHISPERING GALLERY OPTICAL RESONATOR SPECTROSCOPIC PROBE AND METHOD

REFERENCE TO RELATED APPLICATIONS

This application claims priority to and the benefit of provisional application U.S. 61/407,177, filed Oct. 27, 2010, which is hereby incorporated herein by reference in its entirety.

STATEMENT OF GOVERNMENT INTEREST

The invention described hereunder was made in the performance of work under a NASA contract, and is subject to the provisions of Public Law #96-517 (35 U.S.C. 202) in which the Contractor has elected not to retain title.

BACKGROUND

A dielectric material may be shaped to construct an optical whispering-gallery-mode ("WGM") resonator which supports one or more whispering gallery ("WG") modes. These WG modes represent optical fields confined in an interior region close to the surface of the resonator due to the total internal reflection at the boundary. For example, microspheres with diameters from few tens of microns to several hundreds of microns have been used to form compact optical WGM resonators. Such a spherical resonator can include at least a portion of the sphere that comprises the sphere's equator. The resonator dimension is generally much larger than the wavelength of light so that the optical loss due to the finite curvature of the resonators is small. As a result, a high quality factor, Q, may be achieved in such resonators. Some microspheres with sub-millimeter dimensions have been demonstrated to exhibit very high quality factors for light waves, ranging from $10^3$ to $10^9$ for quartz microspheres. Hence, optical energy, once coupled into a whispering gallery mode, can circulate within the WGM resonator with a long photon life time. Such hi-Q WGM resonators may be used in many optical applications, including optical filtering, optical delay, optical sensing, lasers, and opto-electronic oscillators.

A sphere is calculated to sustain a WGM if the internally reflected light returns in phase after a complete orbit. This depends on the spheres diameter and refractive index. An important resonator parameter is the quality factor, or Q-factor and is defined as the ratio $2\Pi(\text{stored energy})/(\text{energy lost per cycle})$. Extremely strong confinement of light within the spherical cavity is possible with Q-factors of up to $10^{10}$. In addition to the high photon densities in the mode volumes, there are intense evanescent fields in proximity to the outer surfaces. The utility of using a resonance tuned microsphere is the excitation photon has increased probability of interaction with a surface analyte as it orbits the sphere many thousands of cycles thus having a higher probability of generating Raman photons or infrared absorptions.

The field of Surface Enhanced Raman Spectroscopy (SERS) has grown considerably since the discovery that a Raman signal can be greatly enhanced for molecules absorbed on special metallic nano-structures and particles. The discipline has expanded to include Surface Enhanced Infrared Absorption (SEIRA) and is now more generally referred to as Surface Enhanced Spectroscopy. In conventional SERS and SEIRA, the signal enhancement is mediated by a plasmon resonance mechanism based on metallic particles. Other optical resonance mechanisms have also been used to provide localized field enhancement when special optical structures are illuminated. SEIRA has been produced using a phonon resonance mechanism with dielectric particles. These distinct resonance mechanisms may be coupled together for plasmon-phonon mediated enhancement of the signal. In other hybrid resonance systems, the plasmon based resonance has been coupled to whispering-gallery mode (WGM) resonances of micro-spheres to improve signal enhancement.

U.S. Patent Publication No. 2010/0264300 to Savchenkov et al., which is incorporated by reference herein in its entirety, is generally directed to an optical device including a whispering gallery mode (WGM) optical resonator configured to support one or more whispering gallery modes; and a photodetector optically coupled to an exterior surface of the optical resonator to receive evanescent light from the optical resonator to detect light inside the optical resonator.

Likewise, U.S. Patent Publication No. 2010/0231903 to Sumetsky, which is incorporated by reference herein in its entirety, is generally directed to an optical microresonator configured as an optical microbubble formed along a section of an optical microcapillary. The curvature of the outer surface of the microbubble creates an optical resonator with a geometry that encourages the circulating WGMs to remain confined in the central region of the bubble, creating a high Q optical resonator. The resonator may be tuned by modifying the physical properties of the microbubble, allowing the resonator to be used as an optical filter. The resonator may also be used as a sensor or laser by introducing the material to be sensed (or the active laser material) into the microcapillary along which the microbubble is formed.

L. K. Ausman and G. C. Schatz, The Journal of Chemical Physics, 129, 054704, 2008), (hereinafter "Ausman"), which is incorporated by reference herein in its entirety, report the results of calculations based on the Mie theory to determine the locally enhanced electric fields due to whispering-gallery mode resonances for silica microspheres. The local electric field enhancement is used to determine the surface enhanced Raman scattering enhancement factors for a molecule. They calculated enhancement factors for dielectric spheres with a refractive index of 1.9 and diameters of 10, 20, and 40 microns for wavelengths across the visible spectrum.

The improved sensitivity obtained while using a whispering-gallery mode resonator is well documented, and in some cases may approach detection of a single molecule. Accordingly, whispering-gallery mode resonator's are well suited for trace analysis. However, optical coupling of the whispering-gallery mode resonator to a spectrometer is reported in the art to require physical contact between the optics of the spectrometer and the resonator, or the optics of the spectrometer must be within the evanescent coupling distance of the whispering-gallery mode resonator, typically a distance of less than one wavelength of the light used as incident electromagnetic radiation.

Accordingly, there is a need for a method and apparatus capable of obtaining spectroscopic measurements using whispering-gallery mode resonators which do not require physical contact between the whispering-gallery mode resonator and the optics of the spectrometer.

SUMMARY

In one aspect of the present invention, a spectroscopic probe comprises at least one whispering gallery mode optical resonator disposed on a support, the whispering gallery mode optical resonator comprising a continuous outer surface having a cross section comprising a first diameter and a second diameter, wherein the first diameter is greater than the second diameter.

In another aspect of the present invention, a method of measuring a Raman spectrum of an analyte comprises: disposing the analyte in contact with an external surface of at least one whispering gallery mode optical resonator disposed on a support, wherein the whispering gallery mode optical resonator comprises a continuous outer surface having a cross section comprising a first diameter and a second diameter, wherein the first diameter is greater than the second diameter; disposing the whispering gallery mode optical resonator within the optical path of a Raman spectrometer comprising an outlet source of electromagnetic radiation and an inlet source coupled to a spectroscopic detector, wherein the outlet source of electromagnetic radiation and the inlet source coupled to the spectroscopic detector are each located at a distance away from the outer surface of the whispering gallery mode optical resonator which is greater than the evanescent coupling distance of the whispering gallery mode optical resonator; arranging the whispering gallery mode optical resonator within the optical path to optically couple the whispering gallery mode optical resonator with the electromagnetic radiation emanating from the outlet source of electromagnetic radiation, irradiating the analyte with evanescent radiation from the whispering gallery mode optical resonator; and measuring the Raman spectrum of the analyte with the Raman spectrometer.

In still another aspect of the present invention, a method of measuring an infra-red spectrum of an analyte comprises: disposing the analyte in contact with an external surface of at least one whispering gallery mode optical resonator disposed on a support, wherein the whispering gallery mode optical resonator comprises a continuous outer surface having a cross section comprising a first diameter and a second diameter, wherein the first diameter is greater than the second diameter; disposing the whispering gallery mode optical resonator within the optical path of an infra-red spectrometer comprising an outlet source of electromagnetic radiation and an inlet source coupled to a spectroscopic detector, wherein the outlet source of electromagnetic radiation and the inlet source coupled to the spectroscopic detector are each located at a distance away from the outer surface of the whispering gallery mode optical resonator which is greater than the evanescent coupling distance of the whispering gallery mode optical resonator; arranging the whispering gallery mode optical resonator within the optical path to optically couple the whispering gallery mode optical resonator with the electromagnetic radiation emanating from the outlet source of electromagnetic radiation, irradiating the analyte with evanescent radiation from the whispering gallery mode optical resonator; and measuring the infra-red spectrum of the analyte with the infra-red spectrometer.

The foregoing has outlined the features and technical advantages of the present invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

In the following description, numerous specific details are set forth to provide a thorough understanding of the present invention. However, it will be obvious to those skilled in the art that the present invention may be practiced without such specific details. In other instances, well-known devices have been shown in block diagram form in order not to obscure the present invention in unnecessary detail. For the most part, details unnecessary to obtain a complete understanding of the present invention have been omitted in as much as such details are within the skills of persons of ordinary skill in the relevant art.

In keeping with long-standing patent law convention, the words "a" and "an" when used in the present specification in concert with the word comprising, including the claims, denote "one or more." Description in which the term "comprising" is used may also include more limiting embodiments such as "consisting essentially of" and "consisting of". Unless stated otherwise, the term comprising is used herein for brevity.

Figure 5:
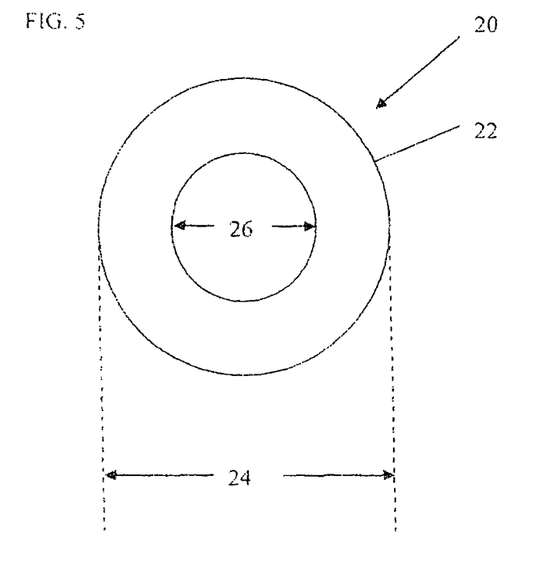
FIG. 5 shows it cross-sectional view of an optical resonator according to an embodiment of the present disclosure.

Broadly, the present invention generally provides a spectroscopic probe comprising at least one whispering gallery mode optical resonator disposed on a support, the whispering gallery mode optical resonator (20) as shown in FIG. 5 comprising a continuous outer surface (22) having a cross section comprising a first diameter (24) and a second diameter (26), wherein the first: diameter (24) is greater than the second diameter (26).

As disclosed herein, surface enhanced Raman scattering has been observed using silica whispering-gallery mode resonators. In an embodiment, the approach demonstrates a Surface enhanced Raman scattering using a non-plasmonic mechanism. The advantages of this non-plasmonic approach disclosed herein include the active substrate is chemically inert, relatively simple to fabricate and the enhancement is broadly applicable across many types of molecular functional groups. In an embodiment, high enhancement factors of greater than or equal to about $10^7$ are observed using 5 micron silica resonators which are not perfect spheres with 785 nm laser excitation.

As discussed above, Ausman et al. have proposed that vary large enhancements are feasible by using 5 micron silica microspheres. Indeed they calculate that enhancement factors that are comparable to those seen from noble metal spheroids are possible enhancements when the Raman scattered radiation also overlaps with a WGM resonance. This is a significant result that indicates that it would be possible to observe SERS with nonresonant scatterers. However, Ausman et al. have limited their calculations to perfect spheres, which require physical contact between optics and the resonators to obtain optical coupling there between.

In an embodiment, very high enhancement factors are shown to indeed be feasible using 5 micron silica microspheres without physical contact between optics and the resonators so long as the spheres are not perfectly spherical. As is further disclosed, an embodiment of the present disclosure is distinct from other work that couples WGM resonance to the plasmon resonance of metallic nano-particles. In an embodiment, no such nano-particles are required herein.

In an embodiment, a spectroscopic probe suitable for use in WGM mediated Surface Enhanced Raman Spectroscopy (WGM-SERS) and/or WGM mediated Surface Enhanced Infra-Red Spectroscopy (WGM-SEIRS) is disclosed using only dielectric spheres. In an embodiment, a method of measuring WGM-SERS and/or WGM-SEIRS is conducted with a spectroscopic probe comprising solid dielectric spheres, which are not perfectly spherical.

The detailed theoretical descriptions of WGM resonators can be found in numerous textbooks and reviews. WGM resonances take place when incident light becomes trapped near the inner surface of a dielectric particle resulting from total internal reflection. The light is trapped in circular orbits as it undergoes multiple total internal reflections at the inner surface of the sphere. This results in enhancement of the evanescent electromagnetic field at certain nodes near the surface of the particle. Internal WGM-SERS has been demonstrated for aerosols and liquid droplets where it is referred to as cavity enhanced Raman (CERS) or morphology-dependent resonances.

In an embodiment, a spectroscopic probe comprises at least one whispering gallery mode optical resonator disposed on a support. In an embodiment, the whispering gallery mode optical resonator comprises a continuous outer surface which is not perfectly spherical. In an embodiment, the outer surface may be continuously non-spherical, e.g., an ellipsoid, or may have a circular cross-section with aberrations or other discontinuous defects in the outer surface such that the cross-section of the outer surface is not a perfect circle, which results in the outer surface being non-spherical.

Accordingly, in an embodiment, the outer surface of the whispering gallery mode optical resonator has a cross section comprising a first diameter and a second diameter, wherein the first diameter is greater than the second diameter. In an embodiment, the outer surface of the whispering gallery mode optical resonator has an elliptical cross section comprising a first diameter and a second diameter, wherein the first diameter is greater than the second diameter. In an embodiment, the first diameter divided by the second diameter is greater than unity (i.e., the first diameter of the resonator is larger than the second diameter of the resonator. In other words, in an embodiment, the outer surface of the whispering gallery mode has an eccentricity which is greater than zero (a perfect sphere has an eccentricity of zero), but less than one (a parabola has an eccentricity of 1).

In an embodiment, the spectroscopic probe comprises a whispering gallery mode optical resonator wherein the outer surface of the whispering gallery mode optical resonator is continuous along all axes. In an embodiment, only a portion of the outer surface of the whispering gallery mode optical resonator is continuous.

In an embodiment, the whispering gallery mode optical resonator is a solid spheroid, or ellipsoid of revolution. Accordingly, in an embodiment, the spectroscopic probe may comprise a whispering gallery mode optical resonator comprising a solid dielectric having an ellipsoid shaped outer surface. In an embodiment, the spectroscopic probe comprises a whispering gallery mode optical resonator comprising silicone dioxide (i.e., quartz), alumina, or a combination thereof, and may be selected based on the wavelength of the radiation to be utilized in the spectroscopic measurement. Silicone dioxide is preferred for Raman spectroscopy and alumina is preferred for infra-red spectroscopy. WGM-SERS may be applied to surface analysis in a manor similar to attenuated total reflectance used in infrared spectroscopy. A micro-manipulator may be used to position the whispering gallery mode optical resonator to areas within an excitation beam of a spectrometer for localized analysis. A similar approach has been used to place SERS active gold colloids using Atomic Force Microscopy. However, in the present disclosure, silica non-perfect spheres or similar surface structures could provide a chemically robust surface for sensor applications that may be cleaned simply by heating. This is an advantage over to conventional gold SERS substrates where the high temperatures (>200 C) necessary for desorption and cleaning of the probe causes diffusion in the gold that degrades the nano-structure required for enhancement. Silver based SERS substrates are limited by the reactivity and long term stability of the silver surface.

In an embodiment, the spectroscopic probe may comprise a whispering gallery mode optical resonator having a hollow chamber disposed within, either completely contained within the resonator, or in fluid communication with an external environment. In an embodiment, the spectroscopic probe may comprise a whispering gallery mode optical resonator comprising a hollow chamber disposed within the spheroid in which an analyte may be circulated through or disposed within for analysis.

In an embodiment, the spectroscopic probe comprises a whispering gallery mode optical resonator having a first diameter suitable to produce whispering gallery mode resonance according to the wavelength of the light being used. In an embodiment, the spectroscopic probe comprises a whispering gallery mode optical resonator having a first diameter greater than or equal to about 0.1 micrometer, preferably greater than or equal to about 1 micrometer, preferably greater than or equal to about 5 micrometers, preferably greater than or equal to about 10 micrometers, preferably greater than or equal to about 20 micrometers, preferably greater than or equal to about 40 micrometers. In an embodiment, the spectroscopic probe comprises a whispering gallery mode optical resonator having a first diameter less than or equal to about 1000 micrometers, preferably less than or equal to about 100 micrometers, preferably less than or equal to about 75 micrometers, preferably less than or equal to about 50 micrometers.

In an embodiment, the spectroscopic probe comprises a whispering gallery mode optical resonator disposed on a support that is dimensioned and arranged to be disposed within the optical path of a microscope coupled to a spectrometer, e.g., a Raman-microscope or an FTIR microscope. Examples of microscopes coupled to spectrometers are well known in the art. Examples include those disclosed in U.S. Patent Application No. 2005/0128476, U.S. Pat. Nos. 4,852,955; 4,843,242; 4,810,093 and the like, which are fully incorporated by reference herein.

In an embodiment, the spectroscopic probe comprises a whispering gallery mode optical resonator having an outer surface which is optically coupleable to a source of electromagnetic radiation and to a spectroscopic detector of a spectrometer, which are each located at a distance from the outer surface of the whispering gallery mode resonator which is greater than the evanescent distance of the whispering gallery mode optical resonator. This may be accomplished in a microscope coupled to a spectrometer. Such microscopes include an outlet source of electromagnetic radiation and an inlet source coupled to a spectroscopic detector of the spectrometer. The arrangement of such components of the microscope vary according to manufacture and the type of measurement being made, and are not limiting in the subject application.

In an embodiment, the whispering gallery mode optical resonator has an outer surface which is optically coupleable to a source of electromagnetic radiation and/or to a spectroscopic detector of a spectrometer, if the whispering gallery mode optical resonator may be arranged with the optical path of a spectrometer, which includes the optical path of a spectroscopic microscope comprising an outlet source of electromagnetic radiation and an inlet source coupled to a spectroscopic detector, wherein irradiation of a portion of the whispering gallery mode resonator with electromagnetic radiation emanating from the outlet source of spectrometer induces whispering gallery mode resonance. In an embodiment, the source of the electromagnetic radiation and the inlet source coupled to the spectroscopic detector are each located at a distance away from the outer surface of the whispering gallery mode optical resonator which is greater than the evanescent coupling distance of the whispering gallery mode optical resonator. Accordingly, in an embodiment, the optics of the spectrometer need not be in physical contact with, or be located within evanescent coupling distance of the whispering gallery mode optical resonator. A resonator which is not perfectly spherical is crucial to the ability to couple the whispering gallery mode optical resonator to the spectrometer at a distance from the outer surface of the whispering gallery mode resonator which is greater than the evanescent distance of the whispering gallery mode optical resonator.

In an embodiment, the spectroscopic probe may comprise a plurality of whispering gallery mode optical resonators, each arranged to be in physical contact with at least one of the other plurality of whispering gallery mode optical resonators. Accordingly, the outer surfaces of the whispering gallery mode optical resonators may be in physical contact, and/or separated by a distance which is less than the evanescent coupling distance of the resonator.

In an embodiment, the spectroscopic probe comprises a support which is at least partially optically transparent. Suitable examples include common microscope slides for Raman measurements. In an embodiment, the spectroscopic probe comprises a reflective support. Reflective supports are preferred for infra-red measurements, and include front surface mirrors in general, and stainless steel mirrors in particular.

Figure 6:
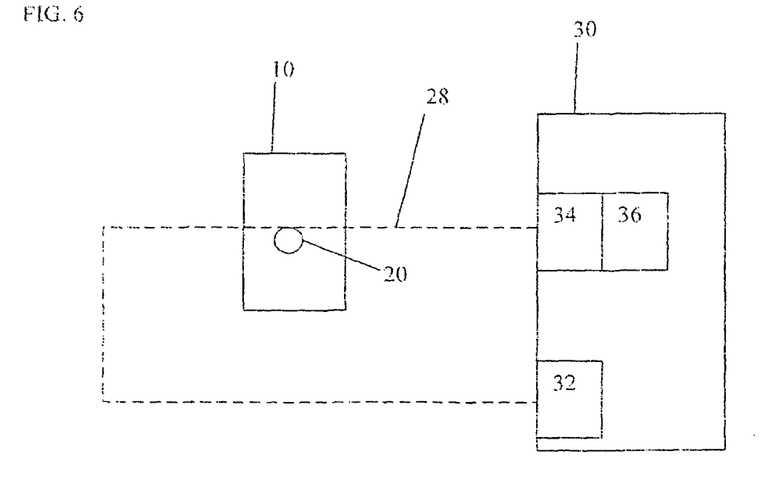
FIG. 6 shows a block diagram of a spectrometer according to an embodiment of the present disclosure.

In an embodiment, a method of measuring a Raman spectrum of an analyte comprises disposing the analyte in contact with an external surface of at least one whispering gallery mode optical resonator disposed on a support, wherein the whispering gallery mode optical resonator comprises a continuous outer surface having an elliptical cross section comprising a first diameter and a second diameter, wherein the first diameter is greater than the second diameter; disposing the whispering gallery mode optical resonator (20, see FIG. 6) within the optical path (28) of a Raman spectrometer (30) comprising an outlet source (32) of electromagnetic radiation and an inlet source (34) coupled to a spectroscopic detector (36), wherein the outlet source of electromagnetic radiation and the inlet source coupled to the spectroscopic detector are each located at a distance away from the outer surface of the whispering gallery mode optical resonator which is greater than the evanescent coupling distance of the whispering gallery mode optical resonator; arranging the whispering gallery mode optical resonator within the optical path to optically couple the whispering gallery mode optical resonator with the electromagnetic radiation emanating from the outlet source of electromagnetic radiation, irradiating the analyte with evanescent radiation from the whispering gallery mode optical resonator; and measuring the Raman spectrum of the analyte with the Raman spectrometer.

In an embodiment, the analyte is disposed in contact with the outer surface of the whispering gallery mode optical resonator as a film having a thickness of less than or equal to about 1 micrometer, i.e., as a thin film. In an embodiment, the analyte may be dissolved or slurried in an appropriate solvent and then a few microliters of the solution may be disposed in contact with the whispering gallery mode optical resonator and the solvent subsequently removed prior to analysis. In an embodiment, the analyte may be applied to produce a film having a thickness of greater than 0.1 nanometers and less than 100 nanometers, preferably less than 10 nanometers, with a thickness from about 1 to 5 nanometers being still more preferred.

In an embodiment, the whispering gallery mode optical resonator is optically coupled to the electromagnetic radiation emanating from the outlet source of electromagnetic radiation within the optical path of a microscope coupled to the Raman spectrometer.

In an embodiment, a method of measuring an infra-red spectrum of an analyte, comprises disposing the analyte in contact with an external surface of at least one whispering gallery mode optical resonator disposed on a support, wherein the whispering gallery mode optical resonator comprises a continuous outer surface having an elliptical cross section comprising a first diameter and a second diameter, wherein the first diameter is greater than the second diameter; disposing the whispering gallery mode optical resonator within the optical path of an infra-red spectrometer comprising an outlet source of electromagnetic radiation and an inlet source coupled to a spectroscopic detector, wherein the outlet source of electromagnetic radiation and the inlet source coupled to the spectroscopic detector are each located at a distance away from the outer surface of the whispering gallery mode optical resonator which is greater than the evanescent coupling distance of the whispering gallery mode optical resonator; arranging the whispering gallery mode optical resonator within the optical path to optically couple the whispering gallery mode optical resonator with the electromagnetic radiation emanating from the outlet source of electromagnetic radiation, irradiating the analyte with evanescent radiation from the whispering gallery mode optical resonator; and measuring the infra-red spectrum of the analyte with the infra-red spectrometer.

In an embodiment, the first diameter of the whispering gallery mode optical resonator is greater than or equal to about 5 micrometers and less than or equal to about 50 micrometers, preferably less than or equal to about 30 micrometers, preferably less than or equal to about 20 micrometers for infra-red spectroscopy.

In an embodiment, the whispering gallery mode optical resonator comprises a solid dielectric having an ellipsoid shaped outer surface, preferably the whispering gallery mode optical resonator comprises alumina for infra-red spectroscopy.

In an embodiment, the analyte is disposed in contact with the outer surface of the whispering gallery mode optical resonator as a film having a thickness of less than or equal to about 1 micrometer. In an embodiment, the analyte may be dissolved or slurried in an appropriate solvent and then a few microliters of the solution may be disposed in contact with the whispering gallery mode optical resonator and the solvent subsequently removed prior to analysis. In an embodiment, the analyte may be applied to produce a film having a thickness of greater than 0.1 nanometers and less than 100 nanometers, preferably less than 10 nanometers, with a thickness from about 1 to 5 nanometers being still more preferred.

In an embodiment, the optical path of the infra-red spectrometer is within a microscope coupled to the infra-red spectrometer.

Figure 1A:
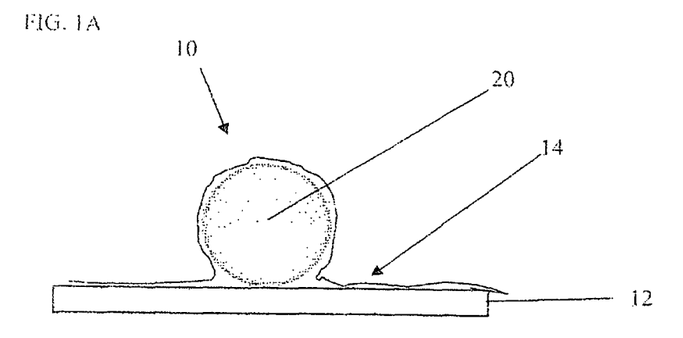
FIG. 1A shows a side view of a spectroscopic probe according to an embodiment of the present disclosure.
Figure 1B:
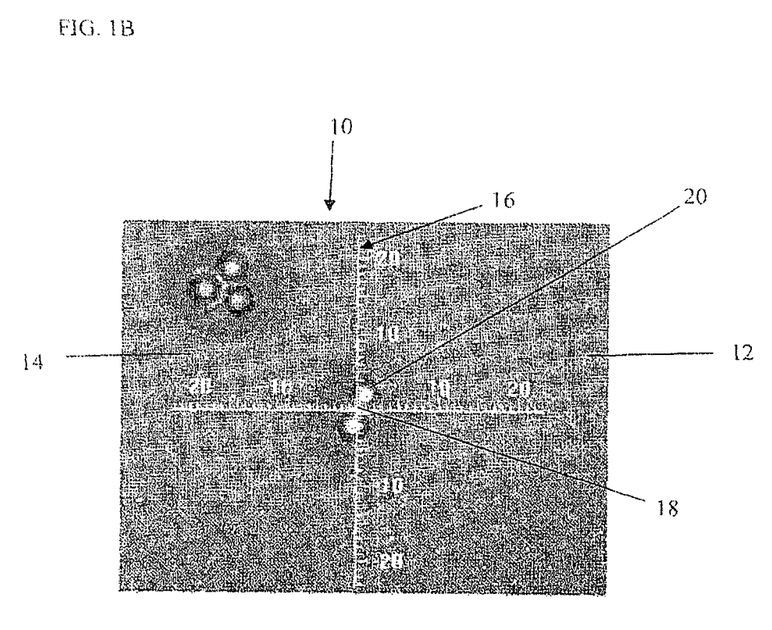
FIG. 1B shows a top view of a spectroscopic probe according to an embodiment of the present disclosure mounted in a spectroscopic microscope according to an embodiment of the present disclosure.

Turning now to the FIGS., FIG. 1A shows an embodiment of the spectroscopic probe, generally labeled 10, which comprises at least one whispering gallery mode optical resonator 20 disposed on a support 12, which may be at least partially covered with a thin layer of analyte 14. As shown in FIG. 1B, a plurality of whispering gallery mode optical resonators 20 are disposed on a support 12, which is at least partially covered with a thin layer of analyte 14. As shown in FIG. 1B, the embodiment of the spectroscopic probe 10 comprises a plurality of whispering gallery mode optical resonators 20 arranged in contact with each other. One of the whispering gallery mode optical resonators 20 is arranged in contact with an excitation source from a spectrometer 18 using a spectroscopic microscope, which is represented by the cross-hairs of the microscope optics 16.

EXAMPLES

Presented here is experimental verification that useful SERS enhancement is feasible with 5-10 micron silica microspheres, which are not perfectly spherical, using a non-plasmonic mechanism. This is distinct from other work that couples plasmon resonance of metallic nano-particles with the WGM of silica particles. Thin films of various compounds coating silica spheres which are not perfectly spherical on a quartz substrate were tested using a Raman microprobe spectrometer. The types of molecules successfully analyzed using this approach are 1,2-di(4-pyridyl)ethylene (BPE), 2-ethyl hexyl phthalate, C60, aliphatic hydrocarbon oil, Carageenan, and Picolinic acid.

The experiments were performed using commercial silica micro-spheres, which are not perfectly spherical (referred to herein as "non-perfect spheres") with average diameters ranging from 5 to 10 microns (Whitehouse Scientific, Cheshire, England). The analytes tested were reagent grade 1,2-di(4-pyridyl)ethylene (BPE, Alpha Aesar), 2-ethyl hexyl phthalate (Kodak), C60 fullerene (Alfa Aesar) and Picolinic acid (Sigma Aldrich).

Several milligrams of the silica non-perfect spheres were placed on a quartz slide and dispersed using a few drops of methanol. The analytes were then cast as thin films using the "drop-drying method" where a dilute methanol solution or slurry of the analyte is deposited with a micro-syringe on to the substrate and the methanol removed by evaporation. This produces thin films in the range of 1 to 5 nanometers thick.

The Raman spectrometer used was a Bruker Senterra equipped with a 785 nanometer excitation laser. The beam intensities were generally set between 10 and 50 mW. The resolution was approximately 9 wavenumbers for broad band measurements and 3-5 wavenumbers for narrow band measurements. The spectra were typically acquired with 10 second integration times and 5 accumulations co-added.

Figure 2:
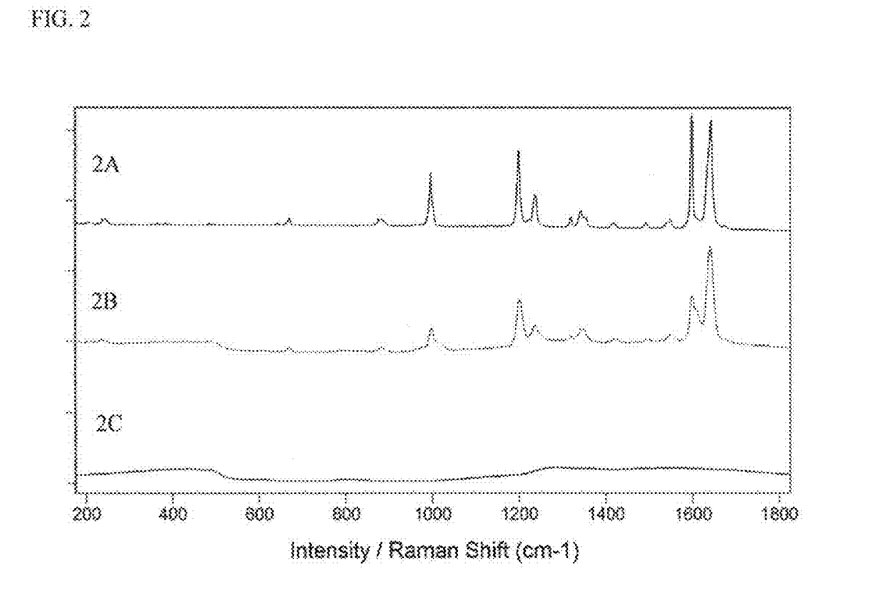
FIG. 2A shows a reference Raman spectrum of an analyte.
FIG. 2B show Raman spectrums of the analyte shown in FIG. 2A, which was obtained according to an embodiment of the present disclosure.
FIG. 2C shows a comparative Raman spectrum of the same analyte shown in FIG. 2B in the absence of an embodiment of the present disclosure.

The laser excitation beam was focused through microscope optics with a beam size of approximately 1 micron. Samples were positioned using a manual microscope x-y stage and the positioning could place the beam approximately on the silica non-perfect sphere but not at a precise location. Typical experiments used isolated or small clusters of 1-3 non-perfect spheres on a quartz substrate. A high Raman signal enhancement was found for the 10 micron diameter non-perfect spheres. The highest enhancement was found for two of the 10 micron non-perfect spheres touching when the beam was focused off center of one of the non-perfect spheres from the microscope optics which spaced at a distance of several millimeters from the surface of the resonators, which is well beyond the evanescent coupling distance of the resonators. A reference KBr thin film Raman measurement of BPE is shown in FIG. 2A. FIG. 2B shows the WGM-SERS spectra of a thin BPE film coating two 10 micron silica non-perfect spheres according to the instant disclosure. As a control, the BPE coated quartz substrate next to the coated non-perfect spheres (approximately 10 microns away). As shown in Comparative FIG. 2C, the measurement did not have a detectable Raman signal from the analyte.

The enhancement can be bound to greater than 1,000. The quantitative amount of signal enhancement is difficult to measure directly because the analyte is undetectable when not on the silica sphere. The estimate is based on the minimum detectable signal of the unenhanced adjacent film on the largest BPE peak.

Figure 3:
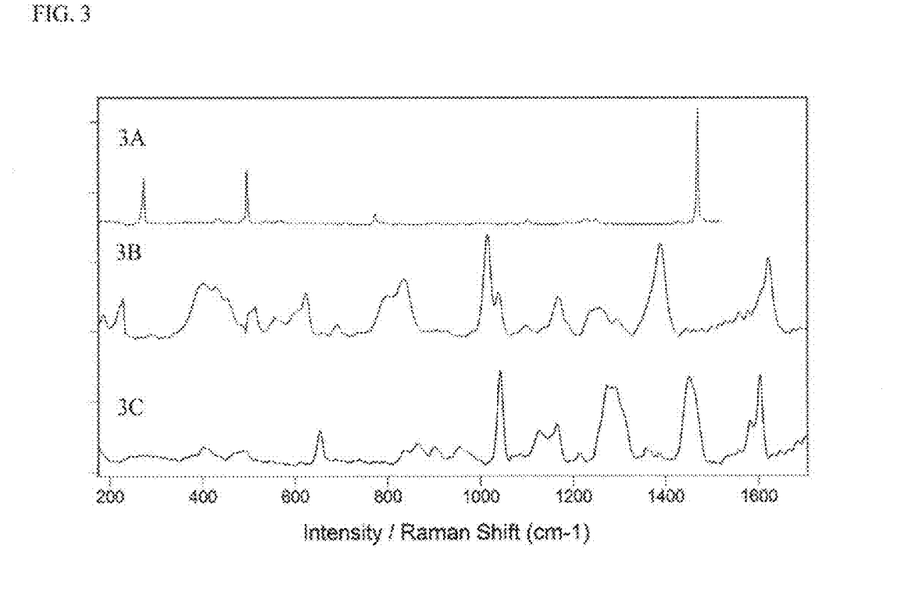
FIGS. 3A, 3B, and 3C show Raman spectrums of analytes which were obtained according to an embodiment of the instant disclosure.

Examples of other compounds measured according to an embodiment of the subject disclosure are given in FIGS. 3A, 3B, and 3C. FIG. 3A shows WGM-SERS of 2-ethyl hexyl phthalate ester according to an embodiment of the instant disclosure; FIG. 3B shows WGM-SERS of C60 fullerene according to an embodiment of the instant disclosure. FIG. 3C shows WGM-SERS of Picolinic acid according to an embodiment of the instant disclosure. There are minor differences observed in some of the WGM-SERS spectra with subtle changes in the peak ratios, peak splitting and the appearance of some minor peaks. This is apparent in the BPE spectrum (FIG. 2) and is also seen in conventional, plasmon mediated, SERS spectroscopy. The enhancement of the pyridine functionalized BPE and the aromatic ester functionalized 2-ethyl hexyl phthalate ester is greater than for the hydrocarbon and silicone compounds. This trend is also observed in conventional, plasmon mediated, SERS spectroscopy.

The enhanced Raman signal was found to be sensitive to positioning and focusing of the laser on the silica non-perfect sphere. The Raman signal enhancement was observed with a range of average particles sizes from 5 to 10 microns in diameter with some sizes off WGM resonance for the excitation beam. The enhancement is the highest when isolated spheres or small clusters are examined and when the beam is focused off center of the non-perfect sphere.

An important result of these examples is the coupling of the excitation beam to the non-perfect sphere. The coupling is influenced by surface defects, surface scattering and interactions with adjacent spheres. There are modes with narrow linewidths that can dominate the internal energy distributions when the incident wave is off resonance. This near resonance dominance may occur when the illuminating beam is Gaussian and focused at the edge of the non-perfect sphere. Since the actual resonators are not perfectly spherical it is postulated that asymmetric resonant modes may be exploited. Asymmetric resonant cavities may undergo "chaos-assisted tunneling", whereby the light rays violate the specular reflection law of ray optics by a small amount and SERS according to the subject disclosure may be used as a probe into this process.

According to an embodiment of the instant disclosure, experiments were performed using commercial 22 micron alumina micro-spheres, which were not perfectly spherical. Alumina non-perfect spheres from were deposited on a stainless steel mirror (~1 mg). This solution with suspended particles was dried with gentle heating over a hot plate. The non-perfect sphere coated SS mirror was then rinsed with DCM several times. The Micro-FTIR spectra were acquired on clusters and individual particles relative to the SS background. The analytes were then cast as thin films using the "drop-drying method" where a dilute methanol solution is deposited with a micro-syringe on to the substrate. This produced a thin film in the range of 1 to 5 nanometers thick.

Figure 4:
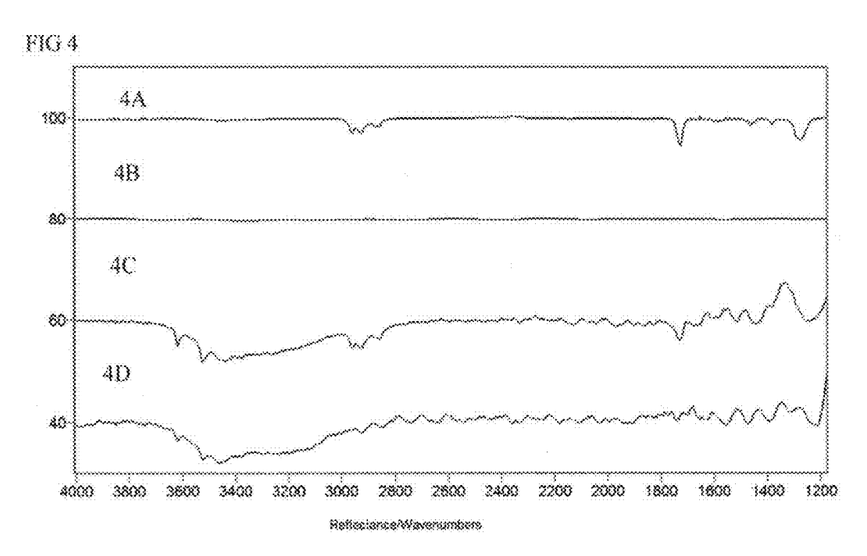
FIG. 4A shows a reference Infra-red spectrum of an analyte.
FIG. 4B shows a comparative Infra-red spectrum of the same analyte shown in FIG. 4A in the absence of an embodiment of the present disclosure.
FIGS. 4C and 4D show Infra-red spectra of the same analyte shown in FIGS. 4A and 4B obtained according to an embodiment of the instant disclosure.

The analytes tested were reagent grade 2-ethyl hexyl phthalate. The spectra were acquired on a Biorad FTS 6000 FTIR with a UMA 600 microscope attachment. The spectroscopic probe according to an embodiment of the present disclosure was arranged using a manual microscope x-y stage and the positioning could place the beam of the spectrometer approximately on the alumina non-perfect spheres but not at a precise location. Typical experiments used isolated or small clusters of 1-3 non-perfect spheres on the reflective substrate. The results are shown in comparative FIG. 4A, which shows the KBr thin film infra-red spectrum of 2-ethyl hexyl phthalate, Comparative FIG. 4B which shows a thin film of the analyte approximately 50 micrometers away from a resonator, FIG. 4C which shows an infra-red spectrum of the analyte according to the present disclosure, wherein an edge of one of a cluster of 4 of the non-perfect spheres were illuminated with the excitation source, and FIG. 4D, wherein another portion of the same cluster of 4 resonators was illuminated.

SEIRA enhancement was evident by the increased infrared absorption of analytes when compared to the same film coating several microns away off the whispering gallery mode optical resonators.

WGM-SEIRS may be considered to be similar to attenuated total reflectance used in infrared spectroscopy. A micromanipulator may be used to position the sphere to areas for localized analysis. A similar approach has been used to place SERS active gold colloids using Atomic Force Microscopy. Alumina spheres or similar dielectric surface structures provide a chemically robust surface for sensor applications that may be cleaned simply by heating.

Accordingly, WGM-SERS based sensors and WGM-SEIRA based sensors using dielectric non-perfect microspheres have been demonstrated using a non-plasmonic mechanism. Enhancements can be used to detect monolayers of films and sub-picogram levels of organic materials not readily detectable using conventional IR or Raman spectroscopy. The method is very simple, only using the non-perfect micro-spheres, a small spatula and a micro-syringe for deposition onto a support.

All patents and publications mentioned in the specification are indicative of the level of those skilled in the art to which the invention pertains. All patents and publications are herein incorporated by reference to the same extent as if each individual publication was specifically and individually indicated to be incorporated by reference.

It should be understood, of course, that the foregoing relates to preferred embodiments of the invention and that modifications may be made without departing from the spirit and scope of the invention as set forth in the following claims.

I claim:

1. A spectroscopic probe for measuring a spectrum of an analyte, comprising:
   at least one whispering gallery mode optical resonator disposed on a support, the whispering gallery mode optical resonator comprising a continuous outer surface having a cross section comprising a first diameter and a second diameter, wherein the first diameter is greater than the second diameter and the analyte is in contact with the outer surface of the optical resonator;
   a spectrometer comprising an outlet source of electromagnetic radiation and an inlet source coupled to a spectroscopic detector, the outlet source and the inlet source are coupled to the spectroscopic detector and are each located at a distance away from the outer surface of the optical resonator which is greater than an evanescent coupling distance of the optical resonator; and,
   wherein the optical resonator is disposed in an optical path of the spectrometer to optically couple the optical resonator with the electromagnetic radiation of the outlet source so that the analyte is irradiated with evanescent radiation from the optical resonator.

2. The spectroscopic probe of claim 1, wherein the spectrometer is selected from the group of an infra-red spectrometer and a Raman spectrometer.

3. The spectroscopic probe of claim 1, wherein the first diameter is greater than or equal to about 5 micrometers and less than or equal to about 50 micrometers.

4. The spectroscopic probe of claim 1, wherein the whispering gallery mode optical resonator comprises a solid dielectric having an ellipsoid shaped outer surface.

5. The spectroscopic probe of claim 1, wherein the whispering gallery mode optical resonator comprises silicone dioxide, alumina, or a combination thereof.

6. The spectroscopic probe of claim 1, comprising a plurality of whispering gallery mode optical resonators, each arranged to be in physical contact with at least one of the other plurality of whispering gallery mode optical resonators.

7. The spectroscopic probe of claim 1, wherein the support is at least partially optically transparent.

8. The spectroscopic probe of claim 1, wherein the support is reflective.

9. A method of measuring a Raman spectrum of an analyte, comprising:
   disposing the analyte in contact with an external surface of at least one whispering gallery mode optical resonator disposed on a support,
   wherein the whispering gallery mode optical resonator comprises a continuous outer surface having a cross section comprising a first diameter and a second diameter, wherein the first diameter is greater than the second diameter;
   disposing the whispering gallery mode optical resonator within the optical path of a Raman spectrometer comprising an outlet source of electromagnetic radiation and an inlet source coupled to a spectroscopic detector, wherein the outlet source of electromagnetic radiation and the inlet source coupled to the spectroscopic detector are each located at a distance away from the outer surface of the whispering gallery mode optical resonator which is greater than the evanescent coupling distance of the whispering gallery mode optical resonator;
arranging the whispering gallery mode optical resonator within the optical path to optically couple the whispering gallery mode optical resonator with the electromagnetic radiation emanating from the outlet source of electromagnetic radiation,
irradiating the analyte with evanescent radiation from the whispering gallery mode optical resonator; and
measuring the Raman spectrum of the analyte with the Raman spectrometer.

10. The method of claim 9, wherein the first diameter is greater than or equal to about 5 micrometers and less than or equal to about 50 micrometers.

11. The method of claim 9, wherein the whispering gallery mode optical resonator comprises a solid dielectric having an ellipsoid shaped outer surface.

12. The method of claim 9, wherein the whispering gallery mode optical resonator comprises silicone dioxide.

13. The method of claim 9, wherein the analyte is disposed in contact with the outer surface of the whispering gallery mode optical resonator is a film having a thickness of less than or equal to about 1 micrometer.

14. The method of claim 9, wherein the whispering gallery mode optical resonator is optically coupled to the electromagnetic radiation emanating from the outlet source of electromagnetic radiation within the optical path of a microscope coupled to the Raman spectrometer.

15. The method of claim 9, wherein the support is at least partially optically transparent.

16. A method of measuring an infra-red spectrum of an analyte, comprising:
disposing the analyte in contact with an external surface of at least one whispering gallery mode optical resonator disposed on a support,
wherein the whispering gallery mode optical resonator comprises a continuous outer surface having a cross section comprising a first diameter and a second diameter, wherein the first diameter is greater than the second diameter;
disposing the whispering gallery mode optical resonator within the optical path of an infra-red spectrometer comprising an outlet source of electromagnetic radiation and an inlet source coupled to a spectroscopic detector, wherein the outlet source of electromagnetic radiation and the inlet source coupled to the spectroscopic detector are each located at a distance away from the outer surface of the whispering gallery mode optical resonator which is greater than the evanescent coupling distance of the whispering gallery mode optical resonator;
arranging the whispering gallery mode optical resonator within the optical path to optically couple the whispering gallery mode optical resonator with the electromagnetic radiation emanating from the outlet source of electromagnetic radiation,
irradiating the analyte with evanescent radiation from the whispering gallery mode optical resonator; and
measuring the infra-red spectrum of the analyte with the infra-red spectrometer.

17. The method of claim 16, wherein the first diameter is greater than or equal to about 5 micrometers and less than or equal to about 50 micrometers.

18. The method of claim 16, wherein the whispering gallery mode optical resonator comprises a solid dielectric having an ellipsoid shaped outer surface.

19. The method of claim 16, wherein the whispering gallery mode optical resonator comprises alumina.

20. The method of claim 16, wherein the analyte is disposed in contact with the outer surface of the whispering gallery mode optical resonator is a film having a thickness of less than or equal to about 1 micrometer.

21. The method of claim 16, wherein the optical path of the infra-red spectrometer is within a microscope coupled to the infra-red spectrometer.

22. The method of claim 16, wherein the support is reflective.

* * * * *